United States Patent
Patel et al.

(10) Patent No.: US 11,699,131 B2
(45) Date of Patent: Jul. 11, 2023

(54) DISTRIBUTED LEDGER SYSTEM FOR AUTOMATED CLAIM ADJUDICATION

(71) Applicant: Synchrony Bank, Stamford, CT (US)

(72) Inventors: Ujjval Patel, Stamford, CT (US); Cheng Hang, Stamford, CT (US); Justin Ruan, Stamford, CT (US)

(73) Assignee: SYNCHRONY BANK, Stamford, CT (US)

(*) Notice: Subject to any disclaimer, the term of this patent is extended or adjusted under 35 U.S.C. 154(b) by 126 days.

(21) Appl. No.: 17/123,743

(22) Filed: Dec. 16, 2020

(65) Prior Publication Data
US 2021/0182793 A1    Jun. 17, 2021

Related U.S. Application Data

(60) Provisional application No. 62/948,511, filed on Dec. 16, 2019.

(51) Int. Cl.
*G06F 16/25* (2019.01)
*G06F 16/27* (2019.01)
(Continued)

(52) U.S. Cl.
CPC ........... *G06Q 10/10* (2013.01); *G06F 16/258* (2019.01); *G06F 16/27* (2019.01); *G06Q 20/389* (2013.01); *G06Q 20/3825* (2013.01); *G06Q 20/40155* (2020.05); *G06Q 40/02* (2013.01); *G06Q 40/04* (2013.01); *G06Q 40/08* (2013.01); *G16H 40/20* (2018.01); *G06Q 30/0185* (2013.01); *G06Q 50/265* (2013.01); *G06Q 2220/00* (2013.01)

(58) Field of Classification Search
CPC ...................................................... G06Q 10/10
See application file for complete search history.

(56) References Cited

U.S. PATENT DOCUMENTS 10,777,879 B2 *  9/2020  Floyd ..................... G06Q 40/08
10,949,926 B1 *  3/2021  Call ....................... G06Q 40/08
(Continued)

OTHER PUBLICATIONS

Acharya, A., "Framework to process high frequency trading using complex event processing," in International Journal of Knowledge Based Computer Systems, vol. 5, Issue 1 (Year: 2017).*

*Primary Examiner* — Olabode Akintola
*Assistant Examiner* — Brandon M Duck
(74) *Attorney, Agent, or Firm* — Polsinelli PC

(57) ABSTRACT

In one aspect, a distributed ledger system include a first network node configured to detect a triggering condition for processing a claim; collect user and broker information for processing the claim; convert the information from a first computer-readable format to a second computer-readable format; validate the converted information based on corresponding digital signatures; generate claim state objects based on the validated information to be used by each node of the distributed ledger system to execute a smart contract for processing the claim; receive one or more updated claim state objects from a second network node reflecting updated processing status of the claim to be used by each node of the distributed ledger system to execute the smart contract for processing the claim; and process the claim based on results of execution of the smart contract using the one or more updated claim state objects.

20 Claims, 5 Drawing Sheets

(51) Int. Cl.
*G06Q 10/10* (2023.01)
*G06Q 20/38* (2012.01)
*G06Q 20/40* (2012.01)
*G06Q 40/02* (2023.01)
*G06Q 40/04* (2012.01)
*G06Q 40/08* (2012.01)
*G16H 40/20* (2018.01)
G06Q 50/26 (2012.01)
G06Q 30/018 (2023.01)

(56) References Cited

U.S. PATENT DOCUMENTS

| | | | |
|---|---|---|---|
| 11,288,736 B1 * | 3/2022 | Jette | G06Q 40/025 |
| 2020/0142984 A1 * | 5/2020 | Miyamoto | G06F 17/30371 |
| 2020/0353937 A1 * | 11/2020 | Bennett | B06W 40/09 |
| 2020/0394915 A1 * | 12/2020 | Salles | G08G 1/16 |
| 2021/0342946 A1 * | 11/2021 | Leise | G06Q 40/08 |

\* cited by examiner

DISTRIBUTED LEDGER SYSTEM FOR AUTOMATED CLAIM ADJUDICATION

CROSS REFERENCE TO RELATED APPLICATIONS

This application claims priority to U.S. Provisional Application 62/948,511 filed on Dec. 16, 2019, the entire content of which is incorporated herein by reference.

BACKGROUND

Field of the Disclosure

The present disclosure relates to a secure system for automated claim adjudication and more specifically, to a secure and tamper proof distributed ledger architecture for recording, monitoring and processing of claims between users, service providers and/or any intermediary broker node.

Description of the Related Art

Adjudication of claims particularly claims arising from interactions and dealings between a user and a service provider, often involve multiple intermediary parties that result in the processing of such claims become time consuming and costly adding significant overhead administrative costs.

Further, deficiencies of legacy systems used in recording, monitoring and processing of such claims present significant risk of breach of privacy of parties involved. This is evidenced by the multi billion dollars insurance fraud that exist, which in turn consumes a lot of law enforcement resources to track and prevent such insurance frauds.

Accordingly, what is needed is a more secure, uniform and cost effective systems for adjudication of claims.

SUMMARY

To address the deficiencies in the existing legacy systems used for recording, monitoring and processing of claims between users, service providers and intermediary brokers as well as to improve the time consuming and costly adjudication process, the present disclosure provides a unique and novel distributed ledger system that detects initiation of a claim adjudication process, extracts necessary information from various sources necessary for creating smart contracts based on which the underlying claim is being adjudicated (using novel and unique APIs and compatible record extraction and conversion codes), and processing the claims. The distributed ledger system and the smart contract provides a secure unified claim adjudication system that can prevent attempted unauthorized access to private user information and resulting fraud.

One aspect of the present disclosure is a distributed ledger system. The distributed ledger system includes a first network node including one or more memories having computer-readable instructions stored therein and one or more processors configured to execute the computer-readable instructions to detect a triggering condition for processing a claim; collect user and broker information for processing the claim; convert the information from a first computer-readable format to a second computer-readable format to yield converted information; validate the converted information based on corresponding digital signatures associated with the converted information to yield validated information; generate claim state objects based on the validated information, the claim state objects being used by each node of the distributed ledger system to execute a smart contract for processing the claim; receive one or more updated claim state objects from a second network node reflecting updated processing status of the claim, the one or more updated claim state objects being used by each node of the distributed ledger system to execute the smart contract for processing the claim; and process the claim based on results of execution of the smart contract using the one or more updated claim state objects.

One aspect of the present disclosure includes one or more non-transitory computer-readable media comprising computer-readable instructions, which when executed by one or more processors of a first node on a distributed ledger system, cause the first node to detect a triggering condition for processing a claim; collect user and broker information for processing the claim; convert the information from a first computer-readable format to a second computer-readable format to yield converted information; validate the converted information based on corresponding digital signatures associated with the converted information to yield validated information; generate claim state objects based on the validated information, the claim state objects being used by each node of the distributed ledger system to execute a smart contract for processing the claim; receive one or more updated claim state objects from a second network node reflecting updated processing status of the claim, the one or more updated claim state objects being used by each node of the distributed ledger system to execute the smart contract for processing the claim; and process the claim based on results of execution of the smart contract using the one or more updated claim state objects.

One aspect of the present disclosure includes a method of automated adjudication of claims on a distributed ledger system. The method includes a method of automated adjudication of claims on a distributed ledger system includes detecting, at a first node of the distributed ledger system, a triggering condition for processing a claim; collecting user and broker information for processing the claim; converting the information from a first computer-readable format to a second computer-readable format to yield converted information; validating the converted information based on corresponding digital signatures associated with the converted information to yield validated information; generating claim state objects based on the validated information, the claim state objects being used by each node of the distributed ledger system to execute a smart contract for processing the claim; receiving one or more updated claim state objects from a second network node reflecting updated processing status of the claim, the one or more updated claim state objects being used by each node of the distributed ledger system to execute the smart contract for processing the claim; and processing the claim based on results of execution of the smart contract using the one or more updated claim state objects.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1A:
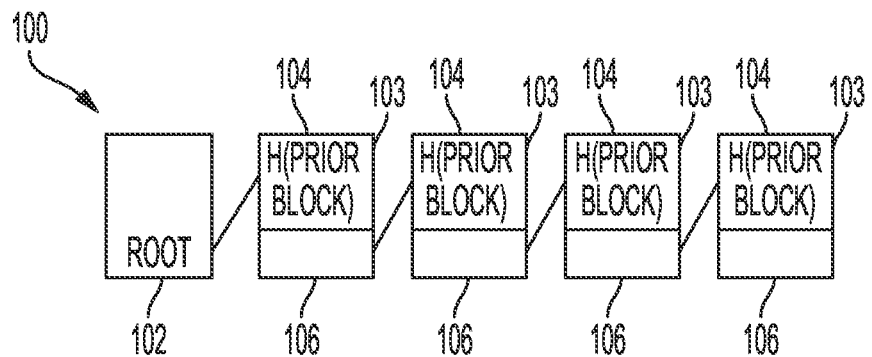
FIGS. 1A-C depict a blockchain network, according to an aspect of the present disclosure.

Specific details are provided in the following description to provide a thorough understanding of embodiments. However, it will be understood by one of ordinary skill in the art that embodiments may be practiced without these specific details. For example, systems may be shown in block diagrams so as not to obscure the embodiments in unnecessary detail. In other instances, well-known processes, structures and techniques may be shown without unnecessary detail in order to avoid obscuring embodiments.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

Example embodiments of the present disclosure will be described more fully hereinafter with reference to the accompanying drawings in which like numerals represent like elements throughout the several figures, and in which example embodiments are shown. Example embodiments of the claims may, however, be embodied in many different forms and should not be construed as limited to the example embodiments set forth herein. The examples set forth herein are non-limiting examples and are merely examples among other possible examples.

As noted above, existing legacy systems for recording, monitoring and processing claims arising from exchanges between parties and potentially any involved third party suffer from many deficiencies such as vulnerability to attacks from unauthorized parties, lack of interoperability of various components thereof and the significant time and cost overhead associated with the processing of such claims. The present disclosure addresses all these problems by providing a distributed ledger based system and network architecture that is secure, is compatible with all existing legacy systems for information retrieval and eliminates time and cost overheads associated with claim processing by providing an automated and seamless processing of claims from initiation to final processing and payment.

One or more examples applications may be described in association with concepts related to adjudication of claims including, but not limited to, dental claims, medical claims, pet insurance claims, etc.

Some aspects of systems and techniques described here provide real time adjudication systems that can result in lower cost overhead, a simplified platform that reduces wait times and enables faster and more secure exchange of medical services between medical specialists to communicate and service patient needs.

Example embodiments described here utilize configured blockchain networks. Through the use of specialized smart contracts, such blockchain network is able to verify and enforce the obligations of the user (e.g., a patient) and the provider without the need for external interference, therefore simplifying the claim adjudication process. Smart contracts may be executed/carried out through computer-based resolutions. In a smart contract, the terms of an underlying insurance claim are outlined. Since an individual's insurance policy is available to the system, the insurance claim may be automatically analyzed by the blockchain system. Any payment for settlement of the insurance claim is automatically processed, thus providing a completely automated and secure system for real-time processing of medical insurance claims.

This real-time claim adjudication system can provide an added advantage of enabling users (e.g., patients) and system operators/medical professional service providers to receive live status updates of planned procedures in near real time.

Moreover, the real-time blockchain based claim adjudication system provides various security improvements over existing platforms and systems used for processing medical claims. For example, whenever a smart contract for an insurance claim is changed/modified, all relevant parties, through associated terminals attached to the blockchain network would be immediately notified on the change thus eliminating any potential unauthorized tampering with an insurance claim and/or underlying patient and service provider information. The system, as described below, provides an improved data security and privacy using a decentralized storage and processing platform. A shared ledger provides an independent and secure platform independently verifiable by all relevant parties to a given medical insurance claim. The decentralized nature of example claim adjudication systems described herein can significantly improve fraud prevention due to the secured exchange of data (e.g., through the use of "blocks" associated with contracts and chronological maintenance of hash values of such "blocks") and independent verification of the blockchain by all relevant parties (e.g., through their respective nodes on the blockchain with insurers, medical service providers and/or patients all having their respective nodes on the blockchain network).

The disclosure begins with a description of an example distributed ledger system (DLT) that can be used to implement the concepts described in the present disclosure. While one example of such DLT is described below, the present disclosure is not limited to this particular DLT and any other known or to be developed DLTs may be used as well.

Figure 1B:
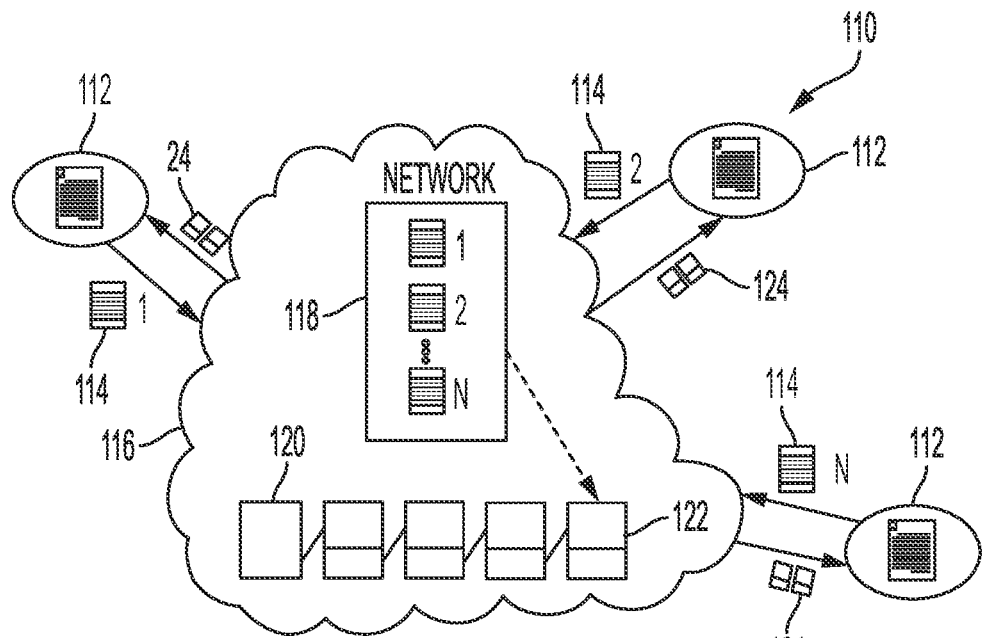
Figure 1C:
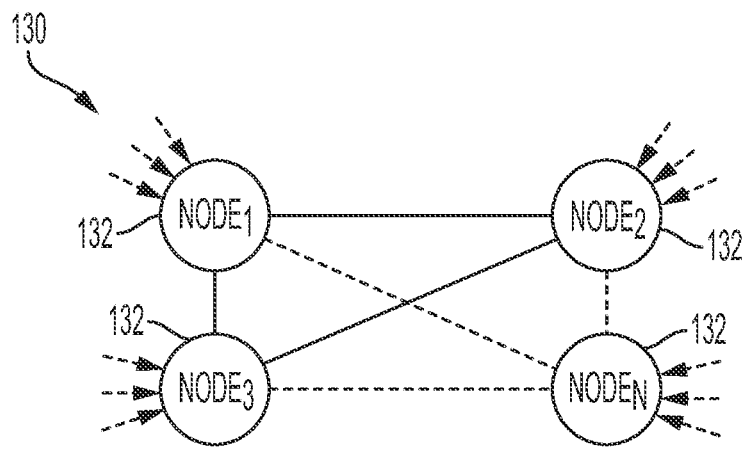

FIGS. 1A-C depict a blockchain network, according to an aspect of the present disclosure. In particular, FIG. 1A illustrates a blockchain data structure 100 made up of a sequence of linked block data structures. A root block 102 typically forms the basis, sometimes referred to as a genesis block, for a blockchain data structure 100. In some aspects, the root block 102 can be a completely self-sufficient seed for an entirely new blockchain data structure 100. For example, the root block 102 of the blockchain does not reference a preceding block and is the original seed from which the blockchain eventually grew. In some other aspects, the root block 102 may be constructed on top of another, already existing blockchain network (e.g., Ethereum, etc.) as a token in order to leverage an existing environment or other features of the underlying network.

The root block 102 typically includes contextual information, but can also include other useful information for downstream blocks 103 or participants and/or observers of the blockchain data structure 100 such as user and service provider identifying information, information about services provided by such service provider, insurance policy guidelines and information, and the like. The blocks 103 may typically be cryptographically linked, directly and indirectly, to the root block 102 via respective headers 104 which each contain a hash of the preceding block 103 or root block 102, as appropriate.

A hash refers to the output of an algorithm which may produce a unique, consistent value based on an input with relatively low risk of collision (e.g., two inputs producing the same output). For example, and without imputing limitation, using the common SHA-256 hashing algorithm on the phrase "genesis node" produces the value: 7856FF57093221558352BDF4D55531D4FCD72BF 7CC8BFFBB86E527606A453B9E.

Where the hash is of the preceding block 103 (as compared to where the root block 102 is the preceding block), the respective hash will include the hash contained in the preceding header 104 of the preceding block 103. While cryptography is more widely known for obfuscating data, in the context of a blockchain, a cryptographic hash is used to validate the veracity of the contents of the previous block based on the low risk of collision and the straightforward reproducibility of attempting to reproduce the hash. In other words, any given block can be checked for alteration by simply producing a hash of it and comparing that hash with the hash stored by the block following it. For example, the hash generated above will always be produced from the phrase "genesis node." However, should the phrase "node genesis" be hashed instead, the hash value will be: E4AFE39853B29E37A44648B9BF376801DCF90204- 2CD894BD04170F919F979479F. Thus, it is merely a matter of reproducing a hash of the contents and comparing against the later recorded hash to verify the authenticity of contents 106 of a block.

The contents 106 of the blocks 103 in a blockchain 100 may contain virtually any type of data. However, as depicted by FIG. 1B, programmable data records, such as one or more smart contracts 114, can be stored as the block content 106. For example, a network 116 may construct a new block 118 containing N, or an arbitrary number of, smart contracts 114. The smart contracts 214 typically represent an automated agreement 112 constructed before being provided to the network 116 for recordation and execution. In response, the network 116 can provide a return portion 124 of an updated blockchain 120 including an appended block 122 (which corresponds to the new block 118).

Typically, the new block 118 can be a node network 130, as depicted by FIG. 1C. The node network 130 itself may include a multitude of nodes 132 which are responsible for maintaining and authenticating the blockchain 100 by receiving material for updates (such as automated contracts 112) from users. In some aspects, the nodes 132 may require consensus between all N nodes, or a majority of nodes, to validate a new block 118 before an updated blockchain portion 124 may be distributed back to users. In some embodiments, nodes 132 may engage in a race to update the blockchain such as by producing a proof of work such as, for example, solving a puzzle that is difficult to solve but easy to verify (for example, by determining a value which produces a hash of the intended new block having specified characteristics, such as a particular number of leading 0s). In some examples, a proof of stake or other proof may be required for a node 132 to update the blockchain 100. In yet other examples, the nodes 132 may perform the process of executing any programmatic contents of the new block 118, such as when the new block contains a smart contract.

With a non-limiting example of a blockchain network described with reference to FIGS. 1A-C, the use of such network within an example system environment of the present disclosure for recording, monitoring and processing of claims between users, service providers and/or any intermediary broker node will now be described with reference to FIG. 2.

Figure 2:
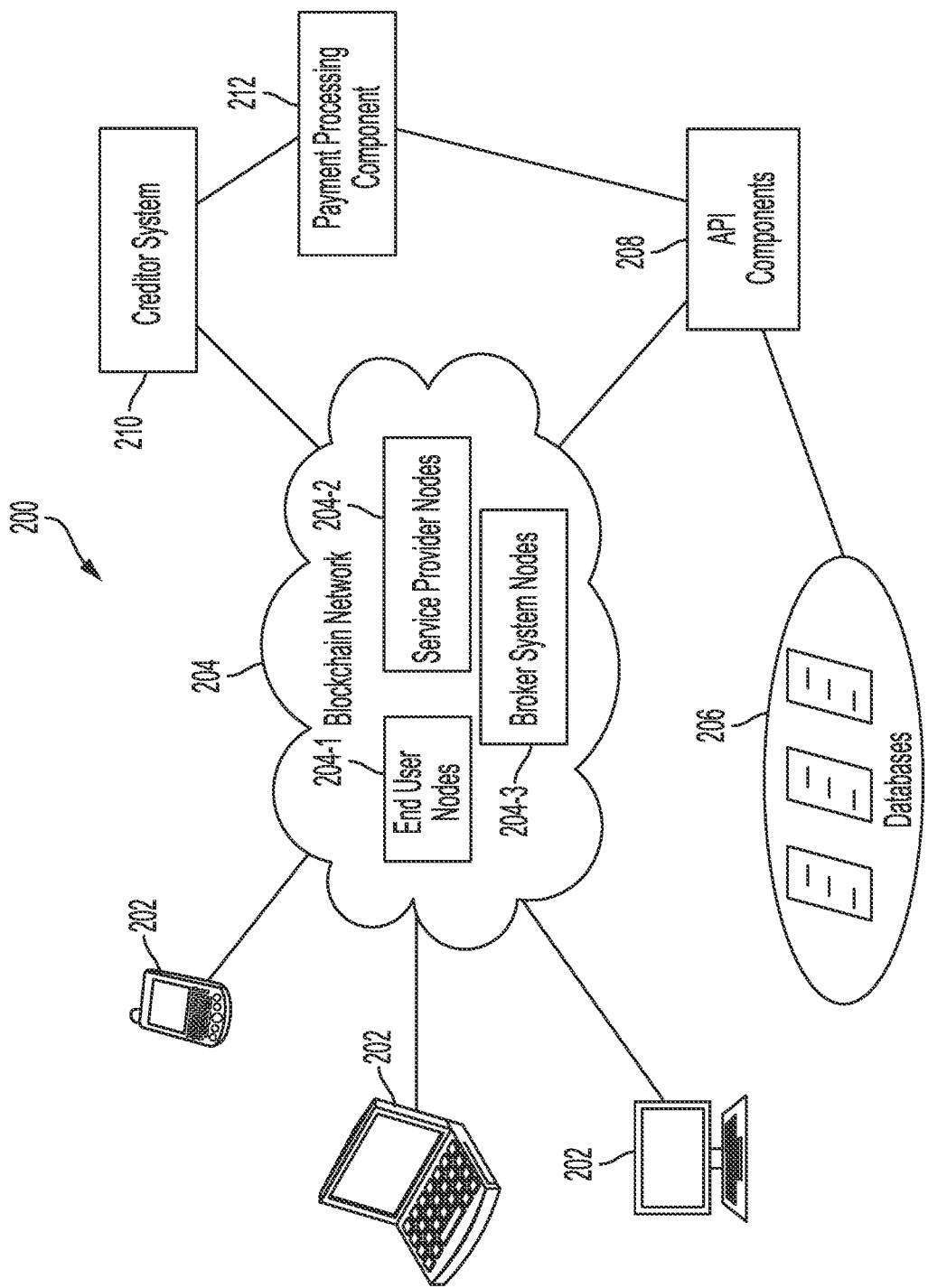
FIG. 2 illustrates an example system environment, according to an aspect of the present disclosure.

FIG. 2 illustrates an example system environment, according to an aspect of the present disclosure. System 200 includes multiple user equipment 202, a blockchain network 204, databases 206, Application Programming Interface (API) components 208, broker systems 210 and a payment processing component 212.

User equipment 202 can be any one of a mobile device, a laptop, a desktop computer as shown in FIG. 2 or any other type of known or to be developed electronic device capable of establishing wired and/or wireless communication session with other remote devices such as databases 206, blockchain network 204, API components 208, creditor system 210, payment processing component 212, etc.

While FIG. 2 illustrates only three user equipment 202, the present disclosure is not limited thereto and system 200 may in fact include hundreds or thousands of end user equipment 202, each of which may be associated with a customer/patient, a service provider such as a dental service provider, a broker such as an insurance provider, etc.

Each of user equipment 202 and its associated entity (patient, service provider, insurer, etc.) may be associated with one node on blockchain network 204 such as one of nodes 130 described above with reference to FIG. 1C.

Blockchain network 204 may be any known or to be developed distributed ledger system including, but not limited to, the example blockchain network of FIGS. 1A-C. Hence, configuration of blockchain network 204 will not be described further for sake of brevity. Blockchain network 204 may have three types of nodes, namely end users node 204-1 (e.g., associated with a patient, a pet, etc.), a service provider node 204-2 (e.g., associated with dental service provider, or a veterinarian or a medical service provider) and broker system nodes 204-3 (e.g., associated with a dental insurance provider, a medical insurance provider, a pet insurance provider, etc.).

In one example, each patient node 204-1 may hold information for corresponding user including identifying information (e.g., name, birth date, social security number, etc.), as other information including, but not limited to, health insurance identification information (e.g., health care identification number, policy number, etc.), one or more claims (past and/or present) associated with the corresponding user, currently active smart contracts being processed on blockchain 204, etc.

In one example, each service provider node 204-2 may hold information for corresponding service provider including provider's identification information, business identification number, information on broker's or insurance providers of which the service provider is a participant, accepted forms of payment, one or more claims (past and/or present) associated with the corresponding service provider, currently active smart contracts being processed on blockchain 204, etc.

In one example, each broker system node 204-3 may be corresponding broker (e.g., insurance provider) including types of offered plans, identification information, one or more claims (past and/or present) being adjudicated/payed for by the corresponding broker, currently active smart contracts being processed on blockchain 204, etc.

As will be described in more detail below, blockchain network 204 may be configured to, upon detecting, initiation of a claim adjudication process, extracts necessary information from various sources (e.g., databases associated 206 with user equipment 202, databases 206, API components 208, and creditors system 210) for creating smart contracts based on which the underlying claim is adjudicated (using novel and unique APIs and compatible record extraction and conversion codes), and processing the claims.

Databases 206 may include one or more connected and/or independent databases, each of which may store one or more sets of data for different nodes of blockchain 204. For example, when a user (e.g., a patient) registers with blockchain network 204, he or she may provide personal, medical/ insurance and/or financial identification information which may be stored in one of databases 206. Similarly service providers and or brokers such as insurers may each have identifying and financial information stored in one or more of databases 206. Another type of data stored in one or more of databases 206 may be insurance data of each user/patient as well as insurance data of each service provider.

API components 208 may include various APIs that may interface with user equipment 202, databases 206, creditor system 210 and/or payment processing component 212 to perform various types of data extraction, conversion and analysis to collect necessary data for creating smart contracts and executing the same on blockchain network 204, as will be more fully described below. API components 208 may also include APIs to interface with broker systems 210 and payment processing component 212 to facilitate execution of smart contracts and payment processing as will be described below.

Broker systems 210 may include one or more financial vehicles/institutions owned by or licensed to pay medical bills on behalf of insured patients and users and may be operated by a broker such as health services provider (e.g., an insurance provider), a broker facilitating the automated/ distributed ledger based system for claim adjudication, etc.

Payment processing component 212 may be any type of known or to be developed external mobile/online payment processing service provider that may be utilized for processing payments for any particular claim that is being automatically adjudicated using distributed ledger system 200 of FIG. 2.

With non-limiting examples of blockchain networks and distributed ledger systems of FIGS. 1 and 2, the disclosure now turns to providing example descriptions of using such systems to automatically adjudicate a claim. Furthermore, a non-limiting everyday application of such process can be an adjudication of a claim arising from a service provided by a dental service provider (e.g., a dentist) to a patient, which will be used below for description purposes. However, applications of such process is not limited to a claim adjudication between a patient and a dentist but can include any other medically or non-medically related claim adjudication between a service user, a service provider and a broker system facilitating payment and coverage for the underlying claim.

Prior to initiating a claim adjudication process per FIG. 4, as will be described below, a non-limiting example process of on-boarding end users 204-1, service providers 204-2 and broker systems 204-3 on blockchain 204 (a distributed ledger on-boarding process) will be described with reference to FIG. 3

Figure 3:
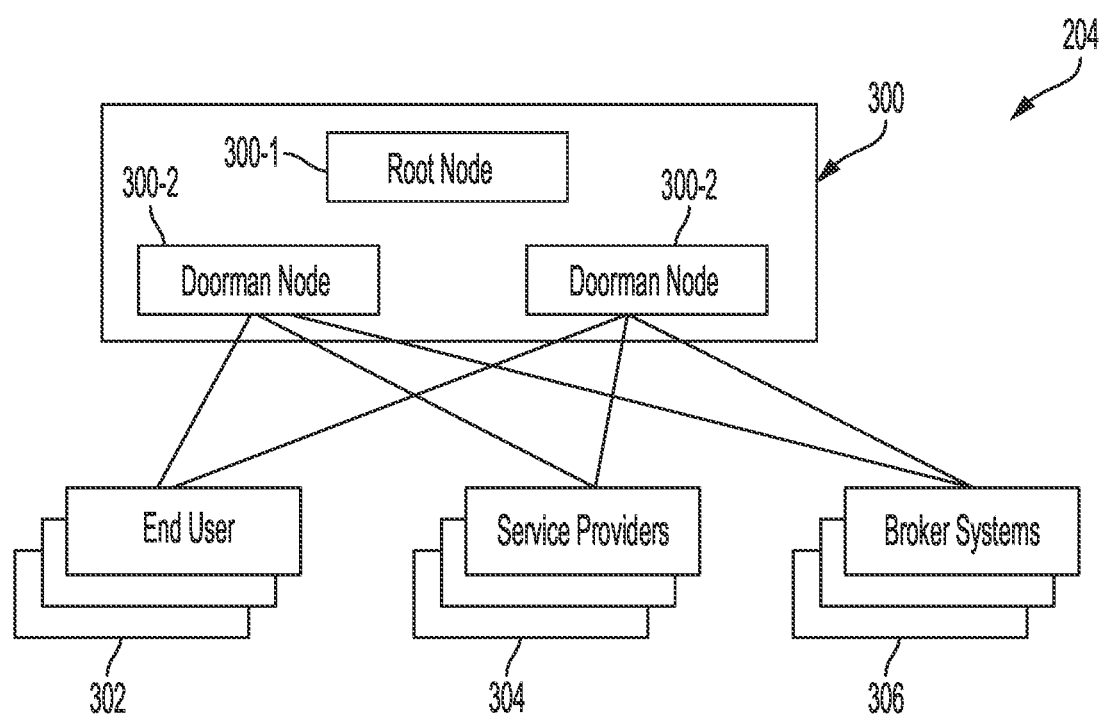
FIG. 3 describes a distributed ledger on-boarding process, according to an aspect of the present disclosure.

FIG. 3 describes a distributed ledger on-boarding process, according to an aspect of the present disclosure.

As can be seen from FIG. 3, blockchain network 204 may have a management component 300. Such management component 300, among other known or to be developed components, may include one or more root nodes 300-1 and one or more doorman nodes 300-2 which work in concert to on-board and certify end users 302, service providers 304 and broker systems 306, all of which may be as described above and may be referred to as requesting nodes (nodes requesting to be on-boarded onto blockchain network 204).

Blockchain network 204 may include three types of Certificate Authorities (CA). Root CA defined and held by root node 300-1, doorman CA held by one or more doorman nodes 300-2 and node CA held by each node of blockchain network 204.

A root CA may define the extent of on-boarding requesting nodes. Doorman CA may be used instead of the root CA for day-to-day key signing (onboarding) to reduce the risk of the root network CA's private key being compromised. Node CA may be used by each respective node for issuing child certificates to sign its identity keys and Transport Layer Security (TLS) certificates. TLS Certificates are used to authenticate the identity of the corresponding certificate holder, and contain a public key which is used to encrypt data before sending data to other nodes in the network.

In one example, each requesting node may initially register with one of doorman nodes 300-2 by submitting a certificate signing request (CSR) to obtain a valid identity. This process may only be necessary when a requesting node connects to blockchain network 204 for the first time, or when the certificate expires (CAs may have an expiration date and can be renewed or new ones can be issued by root node 300-1). There is made possible via a request/response feature built into each requesting node. In another example, the signup process can be done outside of the network via email or a web form.

Upon successful signup of a requesting node such as one of nodes 302, 304 and/or 306, a new node (e.g., one of nodes 204-1, 204-2 or 204-3 will be instantiated on the blockchain network 204 representing a participating node (patient, insurer, provider). In one example, each node may be granted access to other nodes that it is tied to due to the private nature of the blockchain network 204. For instance, a patient covered under insurer A and filing a claim with provider B will only have his/her data read by nodes of blockchain network 204 associated with insurer A and provider B.

In one example, a single entity or business operation may control and operate blockchain network 204 and process of FIG. 3 or alternatively, a consortium of institutions may act in concert to control and operate blockchain network 204.

With an example and non-limiting on-boarding process of FIG. 3 described, the disclosure now turns to a claim adjudication process arising from an interaction or business engagement between an end user and a service provider, where end user's cost for services provided by the service provider may wholly or partially be covered by a broker system such as an insurer.

Figure 4:
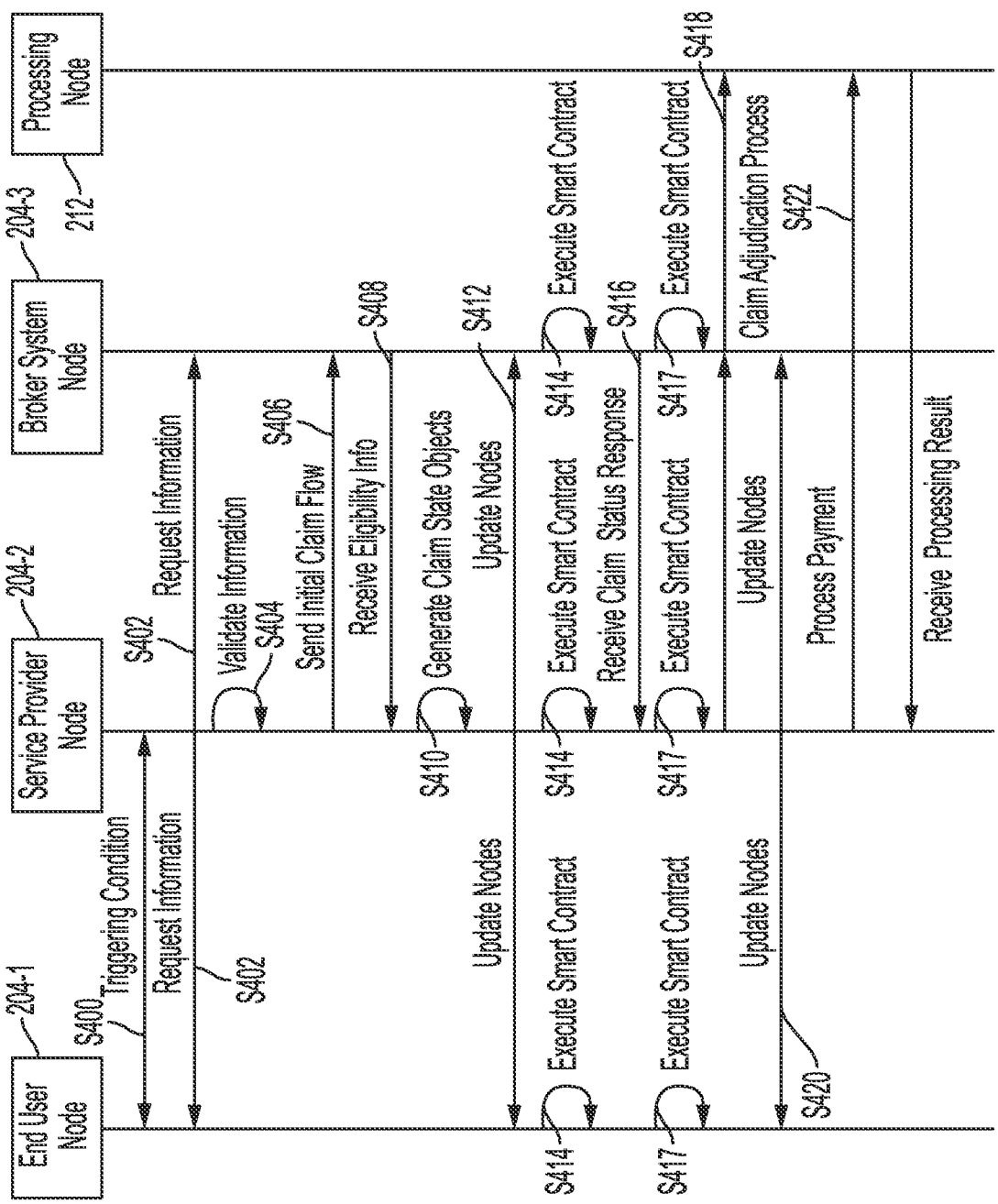
FIG. 4 describes an example claim adjudication process, according to an aspect of the present disclosure.

FIG. 4 describes an example claim adjudication process, according to an aspect of the present disclosure. FIG. 4 will be described with an end user node such as end user node 204-1 (e.g., a patient associated with one of end user nodes 204-1), a service provider node 204-2 (e.g., a dentist associated with one of service provider nodes 204-2), a broker system node 204-3 (e.g., an insurance provider such as one of broker system nodes 204-3) and a processing node such as payment processing component 212 of FIG. 2 as participants in the distributed ledger system 204 of FIG. 2. Each of end user node 204-1, service provider node 204-2 and broker system node 204-3 may be associated with a separate node such as one of nodes 120 of blockchain network 116 described with reference to FIG. 1.

At S400, a triggering condition may be detected. Such triggering condition may be detection of location of an end user equipment 202 associated with end user node 204-1 within premises of service provider associated with service provider node 204-2, within proximity of an end user equipment 202 associated with service provider 204-2, etc. Such detection of proximity may be based on any known or to be developed location determination method such as using Global Positioning System (GPS) coordinates of end user equipment 202 of end user 204-1 and mapping it to known location coordinates of premises of service provider node 204-2 (e.g., known location coordinates of an office of a dentist).

In another example, such location determination may be a proximity based detection whereby one or more on-board sensors of end user equipment 202 of end user 204-1 may communicate with one or more on-site sensors and access points installed on premises of service provider 204-2 (e.g., using a Bluetooth connection, a WiFi connection and/or any other known or to be developed communication method).

In another example, a triggering condition can be user triggered where end user 204-1 may indicate on associated end user equipment 202, his or her presence, initiation of a service by a service provider or a termination of the same (e.g., after a patient leaves the doctor's office). Another user trigger can be initiation of the adjudication process by the service provider once the patient is done with receiving the underlying service, etc.

At S402, service provider node 204-2 may request identifying and insurance information from end user node 204-1 and broker system node 204-3 to initiate a claim creation flow (request user and broker information). Such identifying information may include, but is not limited to, identifying information of user (patient) associated with end user node 204-1, and insurance information of the user. Such information may be stored in and retrieved from one or more relevant databases 206.

In one example, identifying and insurance information of end users and service providers may be stored in one or more databases 206 in any one or more known or to be developed formats including, but not limited to, Electronic Data Interchange (EDI) format.

Service provider node 204-2 may use one or more APIs of API components 208 to convert stored data in databases 206 into compatible format for creating a smart contract. For example, in one aspect, service provider node 204-2 may perform EDI to JSON data conversion on stored patient and service provider identifying and healthcare/insurance information to generate data compatible for generation of smart contracts embodying the underlying claim adjudication process. More specifically, the patient and service provider identifying and healthcare/insurance information may be received as a secure ZIP attachment through a Property Management System (PMS) API, and the initial billable value for services rendered in order to construct an ASC X12: Eligibility, Coverage or Benefit Inquiry form using EDI-JSON that will be sent to the broker system node 204-3, as will be described below. At this stage, using the received patient and service provider information, service provider node 204-2 creates an initial claim flow. An example of a PMS in this context is a software that is executed on terminals associated with service provider node 204-2 and/ or broker system node 204-3 to manage their corresponding operations.

At S404, service provider node 204-2 may validate the information received at S402. For example, each piece of information may be syntax checked or that each piece of identifying and insurance information received at S404 may have been digitally signed using a cryptographic key known to nodes of blockchain 204, as described above with reference to FIG. 3, for example. Accordingly, service provider node 204-2 may validate the digital signature of the received information using the cryptographic key.

At S406, service provider node 204-2 may send the initial claim flow (e.g., identifying the claim to be adjudicated, cost of the claim, patient identifying information, etc.) to broker system node 204-3 (e.g., one of broker system nodes 204-3 of FIG. 2) via an API associated with broker system node 204-3.

At S408, service provider node 204-2 receives, from broker system node 204-3 an ASC X12: Eligibility, Coverage and Benefit information including insurance industry standard codes indicative of coverage level.

At S410, service provider node 204-2 creates one or more claim state objects for adjudicating the claims. Such claim state objects include, but are not limited to, a claim identification, information on services provided, identification of parties to the smart contract (e.g., patient, service provider and broker/insurance provider), insurance coverage, claim status, payable value for the claim, etc.

At S412, service provider node 204-2 updates every node on distributed ledger system (blockchain 204) with the one or more claim state objects.

Upon receiving the one or more claim state objects, at S414, each node on the distributed ledger system (e.g., nodes relevant to the current claim adjudication process such as end user node 204-1, service provider node 204-2, broker system node 204-3 and processing node 212) executes a smart contract using the one or more claim state objects. Therefore, each node on the distributed ledger system will have the most up-to-date state of the claim processing recorded thereon.

Upon executing the smart contract, broker system node 204-3 may call specified smart contract logics unique to the patient's insurer from the received smart contract and verify that the data passed through is in adherence with the insurance agency's policies for the identified patient in the smart contract.

At S416, service provider node 204-2 receives a claim status response from broker system node 204-3 indicating whether the status of service coverage (e.g., whether the patient is fully covered, partially covered or not covered at all for the specific. This response may include on or more updated claim status objects.

At S417, each node on the distributed ledger system (e.g., nodes relevant to the current claim adjudication process such as end user node 204-1, service provider node 204-2, broker system node 204-3 and processing node 212) executes a smart contract (e.g., a different portion of the smart contract than the one executed at S414) using the updated claim state objects provided by broker system node 204-3 at S416.

At S418, service provider node 204-2 performs a claim adjudication process with specific type of adjudication being assigned to the claim based on claim status response received at S324. For example, if claim status response indicates that the end user/patient is fully covered, service provider node 204-2 modifies claim status object in the smart contract to redeemed. If claim status response indicates that the end user/patient is not covered at all, service provider node 204-2 modifies claim status object in the smart contract to billable for out-of-pocket payment by the patient. If claim status response indicates that the end user/patient is partially covered, service provider node 204-2 modifies claim status object to partially redeemed/partially billable.

Accordingly, at S418, the claim status object of the smart contract may be modified to redeemed, billable or partially redeemed/partially billable.

At S420, service provider node 204-2 may update the claim status object of the smart contract to reflect the status assigned at S326 on every node of blockchain network 204.

At S422, service provider node 204-2 may process payment for the claim based on the type of adjudication assigned to the claim at S326.

For example, if the type of claim adjudication assigned to the claim is redeemed (payable by an insurance provider), then at S422, service provider node 204-2, using payment processing node 308 (which may be the same as payment processing node 212) submits a request to insurance provider associated with broker system node 204-3. In submitting this request, service provider node 204-2 may construct a JSON object in the smart contract following ASC X12 and submit the same to broker system node 204-3 for payment. Similarly, when the type of the claim adjudication assigned to the claim is partially billable, service provider node 204-2 may similarly construct a JSON object in the smart contract and submit the same to broker system node 204-3 for partial payment according to the amount redeemable from the insurance provider associated with broker system node 204-3.

In one example, redeeming such payment from the insurance provider may be completed via a payment settler including, but not limited to, Corda Settler accessible via an API of payment processing node 212.

Corda Settler is an application that enables off-ledger payments to be made between parties to any external payment rails (Stripe, Payeezy, etc.). A transaction may be created with service provider node 204-2 and broker system node 204-3 as parties, a notary cluster node for notarizing payment settlement exchanges between the parties, a settlement oracle, an exchange rate oracle and a payment network (e.g., Visa, Mastercard, etc.). This transaction may be cardless as no exchange of physical financial card/account between service provider and insurance provider is needed.

In another example, if the type of claim adjudication assigned to the claim is billable (payable by end user), then at S422, service provider node 204-2, using payment processing node 308 (which may be the same as payment processing node 212) submits a request to end user associated with end user node 204-1 to make payment for the cost of the claim. In submitting this request, service provider node 204-2 may construct a JSON object in the smart contract following ASC X12 and submit the same to end user node 204-1 for payment. Similarly, when the type of the claim adjudication assigned to the claim is partially billable, service provider node 204-2 may similarly construct a JSON object in the smart contract and submit the same to end user node 204-1 for partial payment according to the amount not covered the insurance provider and payable out of pocket by the end user associated with end user node 204-1.

Full or partial billable amount may be processed as a cardless payment transaction where financial information of end user (patient) associated with end user node 204-1 and financial information of service provider node 204-2 may be retrieved from one or more of databases 206. This information may be retrieved and verified in the same manner as identifying and insurance information of end user (patient) and service providers are retrieved at verified at S400 and S412 as described above.

Accordingly, payment processing node 212 may communicate, using secure and cryptographic communication sessions, with relevant financial institutions of patient and service provider on the backend to appropriately charge and credit their accounts for associated cost of the claims.

Example embodiments and concepts described above with reference to FIGS. 1-4 address deficiencies in existing legacy systems used for recording, monitoring and processing of claims between users, service providers and intermediary brokers as well as improve the time consuming and costly adjudication process. These example embodiments and concepts provide a unique and novel distributed ledger system that detects initiation of a claim adjudication process, extracts necessary information from various sources necessary for creating smart contracts based on which the underlying claim is being adjudicated (using novel and unique APIs and compatible record extraction and conversion codes), and processing the claims. The distributed ledger system and the smart contract provides a unified claim adjudication system that is tamper proof and prevents any attempted unauthorized access to private user information and potential fraud related to claim adjudication.

Having described various examples of recording, monitoring and processing of claims between users, service providers and intermediary brokers as well as to improve the time consuming and costly adjudication process, the present disclosure now turns to description of architecture and elements of network components that be utilized to implement the distributed ledger system of FIG. 2 including end user equipment 202, nodes of blockchain network 204, databases 206, API components 208, broker systems 210, etc.

Figure 5:
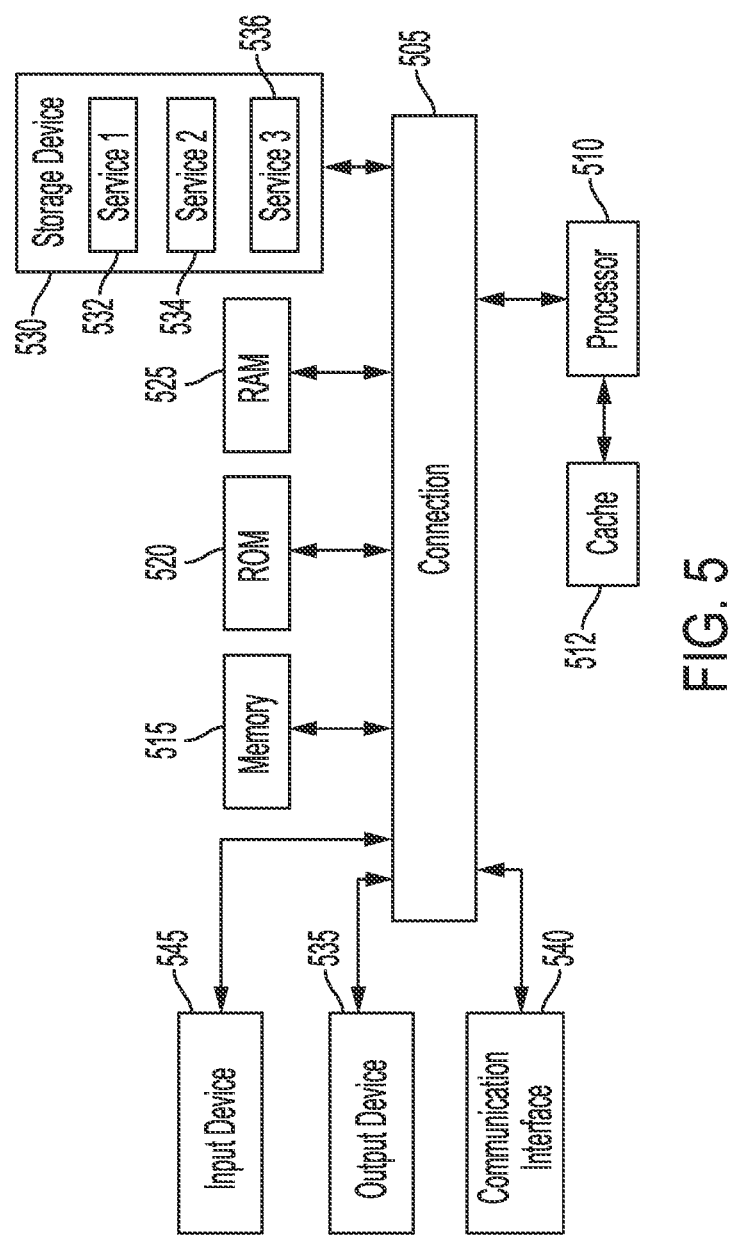
FIG. 5 illustrates example components of a network component, according to an aspect of the present disclosure.

FIG. 5 illustrates example components of a network component, according to an aspect of the present disclosure.

In this example, FIG. 5 illustrates a computing system 500 including components in electrical communication with each other using a connection 505, such as a bus. System 500 includes a processing unit (CPU or processor) 510 and a system connection 505 that couples various system components including the system memory 515, such as read only memory (ROM) 520 and random access memory (RAM) 525, to the processor 510. The system 500 can include a cache of high-speed memory connected directly with, in close proximity to, or integrated as part of the processor 510. The system 500 can copy data from the memory 515 and/or the storage device 530 to the cache 512 for quick access by the processor 510. In this way, the cache can provide a performance boost that avoids processor 510 delays while waiting for data. These and other modules can control or be configured to control the processor 510 to perform various actions. Other system memory 515 may be available for use as well. The memory 515 can include multiple different types of memory with different performance characteristics. The processor 510 can include any general purpose processor and a hardware or software service, such as service 1 532, service 2 534, and service 3 536 stored in storage device 530, configured to control the processor 510 as well as a special-purpose processor where software instructions are incorporated into the actual processor design. The processor 510 may be a completely self-contained computing system, containing multiple cores or processors, a bus, memory controller, cache, etc. A multi-core processor may be symmetric or asymmetric. The storage device 530 can be local and directly attached to connection 505 or can be located far away and communicatively coupled to other components of system 500.

To enable user interaction with system 500, an input device 545 can represent any number of input mechanisms, such as a microphone for speech, a touch-sensitive screen for gesture or graphical input, keyboard, mouse, motion input, speech and so forth. An output device 535 can also be one or more of a number of output mechanisms known to those of skill in the art. In some instances, multimodal systems can enable a user to provide multiple types of input to communicate with system 500. The communications interface 540 can generally govern and manage the user input and system output. There is no restriction on operating on any particular hardware arrangement and therefore the basic features here may easily be substituted for improved hardware or firmware arrangements as they are developed.

Storage device 530 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 525, read only memory (ROM) 520, and hybrids thereof.

The storage device 530 can include services 532, 534, 536 for controlling the processor 510. Other hardware or software modules are contemplated. The storage device 530 can be connected to the system connection 505. In one aspect, a hardware module that performs a particular function can include the software component stored in a computer-readable medium in connection with the necessary hardware components, such as the processor 510, connection 505, output device 535, and so forth, to carry out the function.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" refers to at least one of a set and indicates that one member of the set or multiple members of the set satisfy the claim. For example, claim language reciting "at least one of A and B" means A, B, or A and B.

Example embodiments of the present disclosure may be provided as a computer program product, which may include a computer-readable medium tangibly embodying thereon instructions, which may be used to program a computer (or other electronic devices) to perform a process. The computer-readable medium may include, but is not limited to, fixed (hard) drives, magnetic tape, floppy diskettes, optical disks, compact disc read-only memories (CD-ROMs), and magneto-optical disks, semiconductor memories, such as ROMs, random access memories (RAMs), programmable read-only memories (PROMs), erasable PROMs (EPROMs), electrically erasable PROMs (EE-PROMs), flash memory, magnetic or optical cards, or other type of media/machine-readable medium suitable for storing electronic instructions (e.g., computer programming code, such as software or firmware). Moreover, embodiments of the present disclosure may also be downloaded as one or more computer program products, wherein the program may be transferred from a remote computer to a requesting computer by way of data signals embodied in a carrier wave or other propagation medium via a communication link (e.g., a modem or network connection).

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" a set indicates that one member of the set or multiple members of the set satisfy the claim. For example, claim language reciting "at least one of A and B" means A, B, or A and B.

What is claimed is:

1. A distributed ledger system comprising:
a first network node of a service provider, including one or more memories having computer-readable instructions stored therein and one or more processors configured to execute the computer-readable instructions to:
    detect a triggering condition for real-time processing of a claim, wherein the triggering condition includes automatically detecting a proximity of end user equipment associated with a user and a premises of a service provider;
    collect user information associated with the user and broker information associated with a broker for processing the claim via a smart contract, wherein the user information and broker information are collected by the service provider;
    convert the user information and the broker information from a first computer-readable format to a second computer-readable format to yield converted information, wherein the first computer-readable format is not compatible with the smart contract, and the second computer-readable format is compatible with the smart contract;
    validate the converted information based on corresponding digital signatures associated with the converted information to yield validated information, wherein the corresponding digital signatures are generated using a cryptographic key known to each node of a blockchain associated with the user, the service provider, and the broker;
    generate claim state objects based on the validated information, the claim state objects being used by each node of the distributed ledger system to execute a smart contract for processing the claim;
    receive one or more updated claim state objects from a second network node associated with the broker reflecting updated processing status of the claim, the one or more updated claim state objects being used by each node of the distributed ledger system to execute the smart contract for processing the claim;
    perform a distributed verification of the smart contract execution, wherein the distributed verification is performed by separately by the first network node, the second network node, and the end user equipment; and
    process the claim based on results of execution of the smart contract using the one or more updated claim state objects.

2. The distributed ledger system of claim 1, wherein the triggering condition includes detection of a user terminal within a facility associated with the first network node at a first time and a determination that the user terminal is no longer present at the facility at a second time that is after the first time.

3. The distributed ledger system of claim 1, wherein the first computer-readable format is Electronic Data Interchange (EDI) format and the second computer-readable format is JSON.

4. The distributed ledger system of claim 1, wherein the user information includes user identifying information and user insurance information for processing the claim.

5. The distributed ledger system of claim 1, wherein the first network node is associated with a service provider for which the claim is being processed.

6. The distributed ledger system of claim 5, wherein the second network node is associated with a broker entity providing claim coverage for a user associated with the claim.

7. The distributed ledger system of claim 1, wherein the one or more processors are configured to execute the computer-readable instructions to process the claim by completing a cardless transaction using a financial account of a provider associated with the first network node and at least one of a financial account of an insurance provider associated with the second network node and a financial account of a user who is a party to the claim.

8. The distributed ledger system of claim 1, wherein processing the claim results in a claim status that indicates one of a complete or partial payment for the claim by an entity associated with the second network node.

9. The distributed ledger system of claim 1, wherein the claim is for a dental procedure provided by a provider associated with the first network node.

10. One or more non-transitory computer-readable media comprising computer-readable instructions, which when executed by one or more processors of a first network node on a distributed ledger system, cause the first network node to:
    detect a triggering condition for real-time processing of a claim, wherein the triggering condition includes automatically detecting a proximity of end user equipment associated with a user and a premises of a service provider;
    collect user information associated with the user and broker information associated with a broker for processing the claim via a smart contract, wherein the user information and broker information are collected by the service provider;
    convert the user information and the broker information from a first computer-readable format to a second computer-readable format to yield converted information, wherein the first computer-readable format is not compatible with the smart contract, and the second computer-readable format is compatible with the smart contract;
    validate the converted information based on corresponding digital signatures associated with the converted information to yield validated information, wherein the corresponding digital signatures are generated using a cryptographic key known to each node of a blockchain associated with the user, the service provider, and the broker;
    generate claim state objects based on the validated information, the claim state objects being used by each node of the distributed ledger system to execute a smart contract for processing the claim;
    receive one or more updated claim state objects from a second network node associated with the broker reflecting updated processing status of the claim, the one or more updated claim state objects being used by each node of the distributed ledger system to execute the smart contract for processing the claim;

perform a distributed verification of the smart contract execution, wherein the distributed verification is performed by separately by the first network node, the second network node, and the end user equipment; and process the claim based on results of execution of the smart contract using the one or more updated claim state objects.

11. The one or more non-transitory computer-readable media of claim 10, wherein the triggering condition includes detection of a user terminal within a facility associated with the first network node at a first time and a determination that the user terminal is no longer present at the facility at a second time that is after the first time.

12. The one or more non-transitory computer-readable media of claim 10, wherein the first computer-readable format is Electronic Data Interchange (EDI) format and the second computer-readable format is JSON.

13. The one or more non-transitory computer-readable media of claim 10, wherein the user information includes user identifying information and user insurance information for processing the claim.

14. The one or more non-transitory computer-readable media of claim 10, wherein the first network node is associated with a service provider for which the claim is being processed.

15. The one or more non-transitory computer-readable media of claim 14, wherein the second network node is associated with a broker entity providing claim coverage for a user associated with the claim.

16. The one or more non-transitory computer-readable media of claim 10, wherein the one or more processors are configured to execute the computer-readable instructions to process the claim by completing a cardless transaction using a financial account of a provider associated with the first network node and at least one of a financial account of an insurance provider associated with the second network node and a financial account of a user who is a party to the claim.

17. The one or more non-transitory computer-readable media of claim 10, wherein processing the claim results in a claim status that indicates one of a complete or partial payment for the claim by an entity associated with the second network node.

18. The one or more non-transitory computer-readable media of claim 10, wherein the claim is for a dental procedure provided by a provider associated with the first network node.

19. A method of automated of automated adjudication of claims on a distributed ledger system, the method comprising:

detecting, at a first network node of the distributed ledger system, a triggering condition for real-time processing of a claim, wherein the triggering condition includes automatically detecting a proximity of end user equipment associated with a user and a premises of a service provider;

collecting information associated with the user and broker information associated with a broker for processing the claim via a smart contract, wherein the user information and broker information are collected by the service provider;

converting the user information and the broker information from a first computer-readable format to a second computer-readable format to yield converted information, wherein the first computer-readable format is not compatible with the smart contract, and the second computer-readable format is compatible with the smart contract;

validating the converted information based on corresponding digital signatures associated with the converted information to yield validated information, wherein the corresponding digital signatures are generated using a cryptographic key known to each node of a blockchain associated with the user, the service provider, and the broker;

generating claim state objects based on the validated information, the claim state objects being used by each node of the distributed ledger system to execute a smart contract for processing the claim;

receiving one or more updated claim state objects from a second network node associated with the broker reflecting updated processing status of the claim, the one or more updated claim state objects being used by each node of the distributed ledger system to execute the smart contract for processing the claim;

performing a distributed verification of the smart contract execution, wherein the distributed verification is performed by separately by the first network node, the second network node, and the end user equipment; and processing the claim based on results of execution of the smart contract using the one or more updated claim state objects.

20. The method of claim 19, wherein the triggering condition includes detection of a user terminal within a facility associated with the first network node at a first time and a determination that the user terminal is no longer present at the facility at a second time that is after the first time.

* * * * *